(12) United States Patent
Zhang (10) Patent No.: US 9,482,519 B2
(45) Date of Patent: Nov. 1, 2016

(54) MEASURING SEMICONDUCTOR DEVICE FEATURES USING STEPWISE OPTICAL METROLOGY

(71) Applicant: International Business Machines Corporation, Armonk, NY (US)

(72) Inventor: Yunlin Zhang, Wappingers Falls, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 36 days.

(21) Appl. No.: 14/560,518

(22) Filed: Dec. 4, 2014

(65) Prior Publication Data

US 2016/0161248 A1    Jun. 9, 2016

(51) Int. Cl.
  *G01N 21/47* (2006.01)
  *G01B 11/02* (2006.01)
  *G01B 11/14* (2006.01)

(52) U.S. Cl.
  CPC ............... *G01B 11/14* (2013.01); *G01B 11/02* (2013.01); *G01N 21/4738* (2013.01); *G01N 2201/12* (2013.01)

(58) Field of Classification Search
  CPC .. G01B 11/02; G01B 11/14; G01N 21/4738; G01N 2201/12
  USPC ............ 356/601–625; 430/22, 312, 394
  See application file for complete search history.

(56) References Cited

U.S. PATENT DOCUMENTS

| | | | |
|---|---|---|---|
| 5,745,239 A | 4/1998 | Chen et al. | |
| 5,831,736 A | 11/1998 | Lichtman et al. | |
| 5,999,266 A | 12/1999 | Takahashi et al. | |
| 6,081,325 A | 6/2000 | Leslie et al. | |
| 6,271,047 B1 * | 8/2001 | Ushio | B24B 37/013 257/E21.528 |
| 6,284,465 B1 * | 9/2001 | Wolber | G01N 21/253 250/559.29 |
| 6,313,913 B1 * | 11/2001 | Nakagawa | G01N 21/94 250/225 |
| 6,657,736 B1 | 12/2003 | Finarov et al. | |

(Continued)

FOREIGN PATENT DOCUMENTS

| | | |
|---|---|---|
| EP | 1180660 A3 | 4/2004 |
| WO | 01/97279 A2 | 12/2001 |

(Continued)

OTHER PUBLICATIONS

Attota et al, "Through-focus Scanning Optical Microscopy", Scanning Microscopies 2011, Proc. of SPIE, vol. 8036, 2011 SPIE, doi: 10.1117/12.884706, pp. 803610-1-803610-9.

(Continued)

*Primary Examiner* — Sang Nguyen
(74) *Attorney, Agent, or Firm* — Scully Scott Murphy and Presser; Frank Digiglio (57) ABSTRACT

The present invention relates generally to metrology, and more particularly, to an apparatus and method of measuring multiple parameters of a structure or feature of a semiconductor device using a combination of stepwise optical metrology and a linear system of equations to generate an output as function of position. In an embodiment, a light beam having a width greater than the features to be measured may be shined on a first area of the semiconductor device to calculate a first average. The light beam may then be shined on a second area that overlaps the first area by at least one individual feature to calculate a second average. The averages may be entered into a system of linear equations which may then be solved to calculate an overall average.

17 Claims, 5 Drawing Sheets

(56) References Cited

U.S. PATENT DOCUMENTS

| | | | |
|---|---|---|---|
| 6,750,952 B2* | 6/2004 | Grodnensky | G03F 7/70591 355/52 |
| 6,750,974 B2 | 6/2004 | Svetkoff et al. | |
| 6,767,680 B2* | 7/2004 | Schulz | G03F 7/70633 356/400 |
| 6,791,099 B2 | 9/2004 | Some et al. | |
| 6,858,859 B2 | 2/2005 | Kusunose | |
| 7,126,700 B2 | 10/2006 | Bao et al. | |
| 7,289,214 B1* | 10/2007 | Li | G03F 9/7076 356/401 |
| 7,564,554 B2* | 7/2009 | Weiss | G03F 9/7084 356/401 |
| 7,586,623 B2 | 9/2009 | Bischoff et al. | |
| 7,619,731 B2 | 11/2009 | Lally et al. | |
| 8,393,010 B2 | 3/2013 | Chen et al. | |
| 2002/0158193 A1* | 10/2002 | Sezginer | G03F 7/70633 250/237 G |
| 2003/0224261 A1* | 12/2003 | Schulz | G01B 11/272 430/22 |
| 2005/0021303 A1* | 1/2005 | Matsushita | G11C 29/006 702/185 |
| 2005/0134865 A1* | 6/2005 | Schoonewelle | G03F 9/7011 356/601 |
| 2008/0216863 A1* | 9/2008 | Ettinger | G01P 3/486 134/1 |
| 2013/0132036 A1 | 5/2013 | Saleh | |
| 2013/0136236 A1 | 5/2013 | Morikawa et al. | |

FOREIGN PATENT DOCUMENTS

| | | |
|---|---|---|
| WO | 02/086942 A1 | 10/2002 |
| WO | 02/091248 A1 | 11/2002 |

OTHER PUBLICATIONS

Chao et al, "Method for Quantification of Process Non-Uniformity Using Model-Based Metrology", U.S. Appl. No. 14/077,235, filed Nov. 12, 2013, 18 pages.

* cited by examiner

MEASURING SEMICONDUCTOR DEVICE FEATURES USING STEPWISE OPTICAL METROLOGY

BACKGROUND

The present invention relates generally to metrology and, more particularly, to an apparatus and method of measuring multiple parameters of a structure using stepwise optical metrology and providing measurements of feature variation as a function of position.

Typically, characteristics such as height, width, and location of features of semiconductor devices are measured using two types of metrology techniques: direct and indirect. Direct metrology may use a probe, or in the case of scanning electron microscopy, an electron beam, that is much smaller than the features being measured to render an image of the features. Indirect metrology may use a probe that is much larger than the features being measured and relies on comparing a measured metric, such as the diffraction/reflection of light, collected by the tool to a calibrated value and then extrapolating the difference to give a representation of the desired characteristic.

SUMMARY

According to an embodiment, a method of measuring an average characteristic of features on a semiconductor structure is disclosed. The method may include: projecting an light beam onto the features in a first area; collecting a first reflected light beam from the first area, wherein the first reflected light beam is the projected light beam after it has reflected off the features in the first area; converting the first reflected light beam into first data; projecting the light beam onto the features in a second area, wherein the second area overlaps with the first area by at least one individual feature; collecting a second reflected light beam from the second area, wherein the second reflected light beam is the projected light beam after it has reflected off the features in the second area; converting the second reflected light beam into second data; and performing analysis of the first data and second data. The analysis may include: setting up a first linear equation representing a first weighted average of the characteristic of the features in each of the first area; setting up a second linear equation representing a second weighted average of the characteristic of the features in each of the first area; combining the first linear equation and the second linear equation into a system of equations; and solving the system of equations to determine an overall average.

According to another embodiment, a computer program product for measuring an average characteristic of features on a semiconductor structure is disclosed. The computer program product may include a computer readable storage medium readable by a processing circuit and storing instructions for execution by the processing circuit for performing a method that includes: projecting a light beam onto the features in a first area; collecting a first reflected light beam from the first area, wherein the first reflected light beam is the projected light beam after it has reflected off the features in the first area; converting the first reflected light beam into first data; projecting the light beam onto the features in a second area, wherein the second area overlaps with the first area by at least one individual feature; collecting a second reflected light beam from the second area, wherein the second reflected light beam is the projected light beam after it has reflected off the features in the second area; converting the second reflected light beam into second data; and performing analysis of the first data and second data. The analysis may include: setting up a first linear equation representing a first weighted average of the characteristic of the features in each of the first area; setting up a second linear equation representing a second weighted average of the characteristic of the features in each of the first area; combining the first linear equation and the second linear equation into a system of equations; and solving the system of equations to determine an overall average.

According to another embodiment, a computer system for measuring an average characteristic of features on a semiconductor structure is disclosed. The computer system may include: a memory; a processor in communication with the memory that may include an instruction fetching unit for fetching instructions from memory and one or more execution units for executing fetched instructions. The computer system may be capable of performing a method that includes: projecting a projected light beam onto the features in a first area; collecting a first reflected light beam from the first area, wherein the first reflected light beam is the projected light beam after it has reflected off the features in the first area; converting the first reflected light beam into first data; projecting the light beam onto the features in a second area, wherein the second area overlaps with the first area by at least one individual feature; collecting a second reflected light beam from the second area, wherein the second reflected light beam is the projected light beam after it has reflected off the features in the second area; converting the second reflected light beam into second data; and performing analysis of the first data and second data. The analysis may include: setting up a first linear equation representing a first weighted average of the characteristic of the features in each of the first area; setting up a second linear equation representing a second weighted average of the characteristic of the features in each of the first area; combining the first linear equation and the second linear equation into a system of equations; and solving the system of equations to determine an overall average.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which not all structures may be shown.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art.

For purposes of the description hereinafter, the terms "upper", "lower", "right", "left", "vertical", "horizontal", "top", "bottom", and derivatives thereof shall relate to the disclosed structures and methods, as oriented in the drawing figures. It will be understood that when an element such as a layer, region, or substrate is referred to as being "on", "over", "beneath", "below", or "under" another element, it may be present on or below the other element or intervening elements may also be present. In contrast, when an element is referred to as being "directly on", "directly over", "directly beneath", "directly below", or "directly contacting" another element, there may be no intervening elements present. Furthermore, the terminology used herein is for the purpose of describing particular embodiments only and is not intended to be limiting of the invention. As used herein, the singular forms "a," "an," and "the" are intended to include the plural forms as well, unless the context clearly indicates otherwise.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is rather focused on the distinctive features or elements of various embodiments of the present invention.

The present invention relates generally to metrology, and more particularly, to an apparatus and method of measuring multiple parameters of a structure or feature of a semiconductor device using a combination of stepwise optical metrology and a linear system of equations to generate an output as function of position.

Direct metrology techniques may provide very detailed local information, but the information space is limited. For example, critical dimension scanning electron microscopy can only measure small areas and is limited to top-down measurements. Atomic force microscopy can also only measure small areas and can only provide profile measurement. Inverse metrology techniques may provide information on multiple parameters, such as sidewall angle, thickness, underlying layers, but is considered to be an average over a large area. It is often limited by the physical size of the measurement beam spot, which may be on the order of 25 μm or larger.

Embodiments of the present invention include techniques to evaluate characteristics (e.g., height, width, and location) of structures or features on a wafer (or part of a wafer) during a fabrication process. Embodiments may be incorporated into a model based metrology tool, and more particularly in the software part of the tool, such as a scatterometry tool, an optical critical dimension (OCD) tool, and a model based infra-red (MBIR) tool.

Embodiments may be used to measure features that may occur on the wafer according to a plan. Typically, the features may occur at regular intervals, such as fins in a fin field effect transistor (finFET) device. During typical fabrication, these features may later be covered with additional layers in the process of creating the finished chip. Therefore, the present invention may be used at an intermediate stage of the fabrication process, prior to covering the features with a new layer, in order to test or evaluate the layout. Embodiments by which to provide measurements of multiple parameters at a local level using a single toolset incorporating stepwise optical metrology and a linear system of equations is described below with reference to FIGS. 1-5.

Figure 1A:
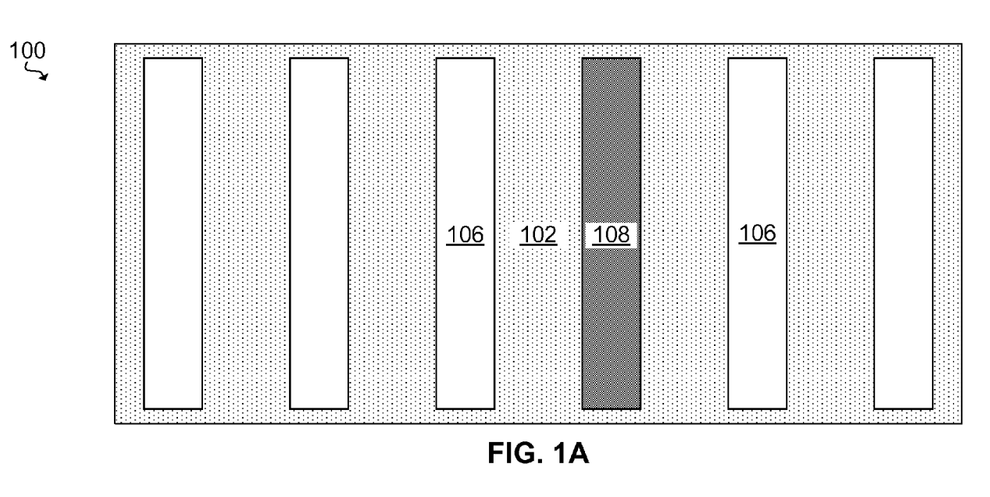
FIG. 1A is a top view and FIG. 1B is a cross section view of a structure 100, according to an embodiment of the present invention.
Figure 1B:
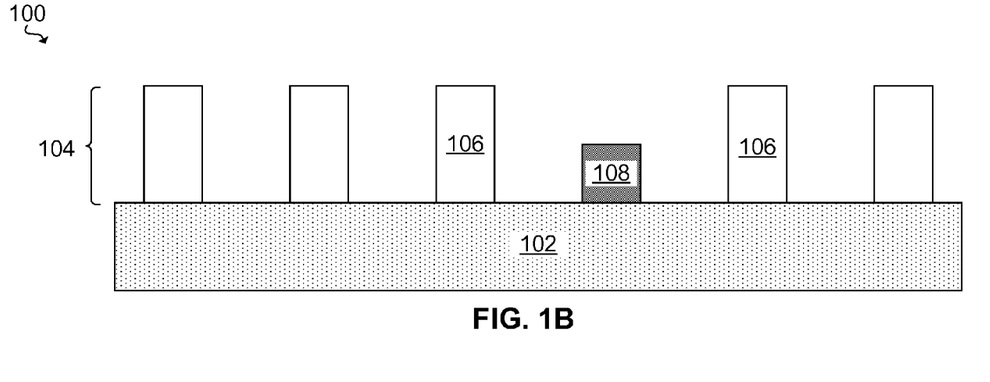

Referring now to FIGS. 1A-1B, a structure 100 is shown. FIG. 1A illustrates a top view of the structure 100 and FIG. 1B illustrates a cross section view of the structure 100. The structure 100 may be a semiconductor device. In an embodiment, the structure 100 may be a fin field effect transistor (finFET) device at a point during fabrication. The structure 100 may include a base substrate 102. The base substrate 102 may be composed of a bulk semiconductor substrate, such as, for example doped or undoped silicon, doped or undoped germanium, or a III-V compound. In an embodiment the base substrate 102 may be composed of a semiconductor on insulator (SOI) substrate that includes a base layer and an insulator layer. In another embodiment, the base substrate 102 may be composed of a dielectric layer, such as, for example, an oxide or nitride.

The structure may also include one or more features formed on the base substrate 102. In an embodiment, the features may be one or more fins 104 (hereinafter "fins"). The fins 104 may be composed of a semiconductor material having a similar or different composition as the base substrate. The fins 104 may be lightly doped with n-type and/or p-type dopants. In an embodiment, the fins 104 may include individual fins having a uniform height. In another embodiment, the fins 104 may be include individual fins having different heights. In such an embodiment, the fins 104 may be composed of one or more tall fins 106 (hereinafter "tall fins") and one or more short fins 108 (hereinafter "short fins"). It should be noted that although only two different fin heights are described below, one of the ordinary skill in the art would understand that the individual fins of the fins 104 may have a range of different heights. In an embodiment, the tall fins 106 may have a height of approximately 10 nm and the short fins 108 may have a height of approximately 5 nm.

Figure 2:
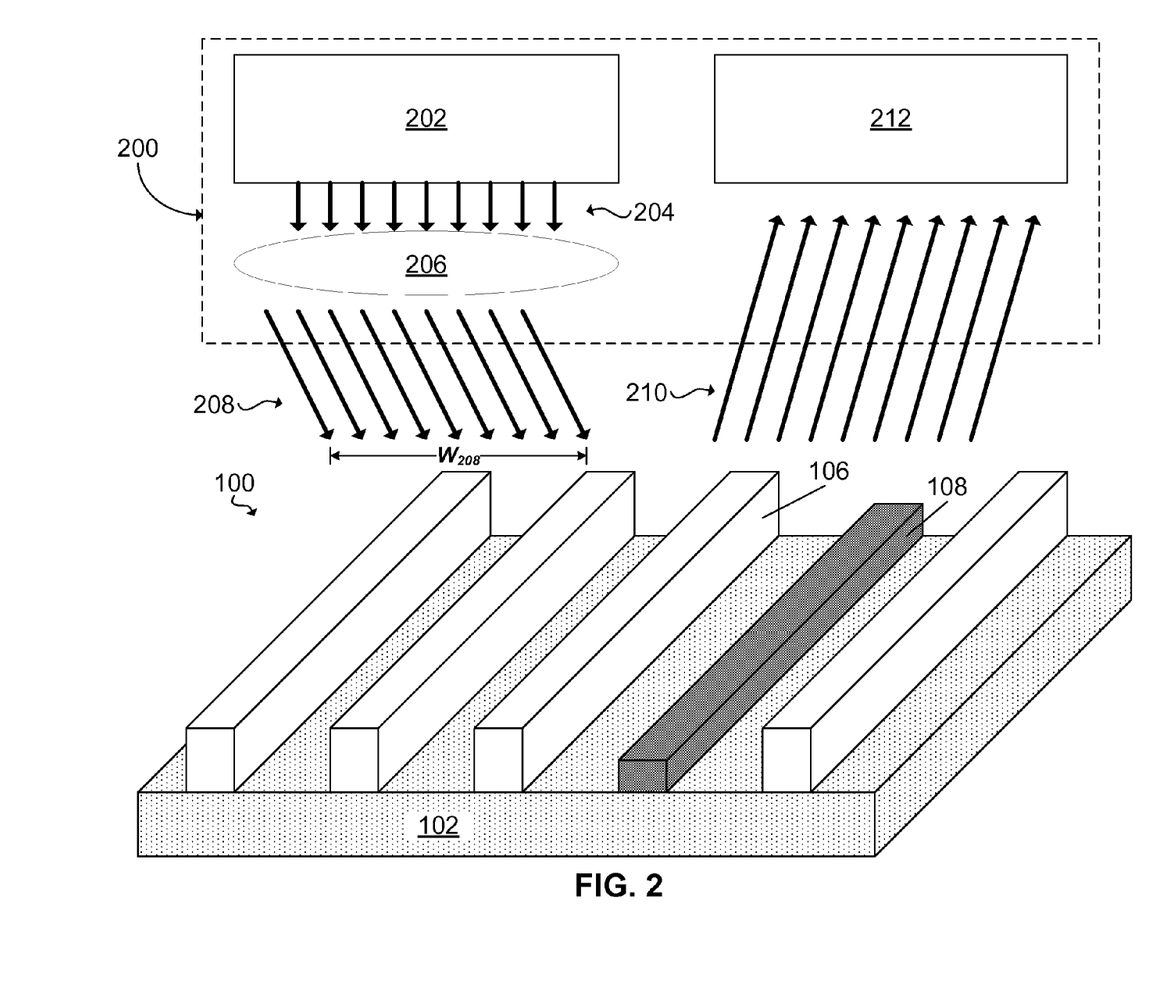
FIG. 2 is an illustrative view of a metrology tool and the structure, according to an embodiment of the present invention.

Referring now to FIG. 2, an illustrative view of a metrology tool 200 and the structure 100 is shown. In an embodiment, the metrology tool 200 may be a conventional inverse metrology probe. The metrology tool 200 may include a light source 202 that emits a source light 204 that may have a wavelength that corresponds to visible light or infrared light. The metrology tool 200 may optionally have a reticle 206 that focuses the source light 204 into an impacting light beam 208. The impacting light beam 208 may strike the surface of the structure 100 and subsequently reflect, refract, diffract, scatter, and/or diffuse off the fins 104 and base substrate 102 as a reflected light beam 210. The reflected light beam 210 may then impact a detector 212 that may include a photodetector to measure the amount of reflection, refraction, diffraction, scattering, and/or diffusion.

The impacting light beam 208 may have a width $W_{208}$ that is typical in the art. The width $W_{208}$ may be greater than the spacing between the fins 104, but less than an entire area to be scanned. In an embodiment, the width $W_{208}$ may range from approximately 10 μm to approximately 50 μm.

Figure 3A:
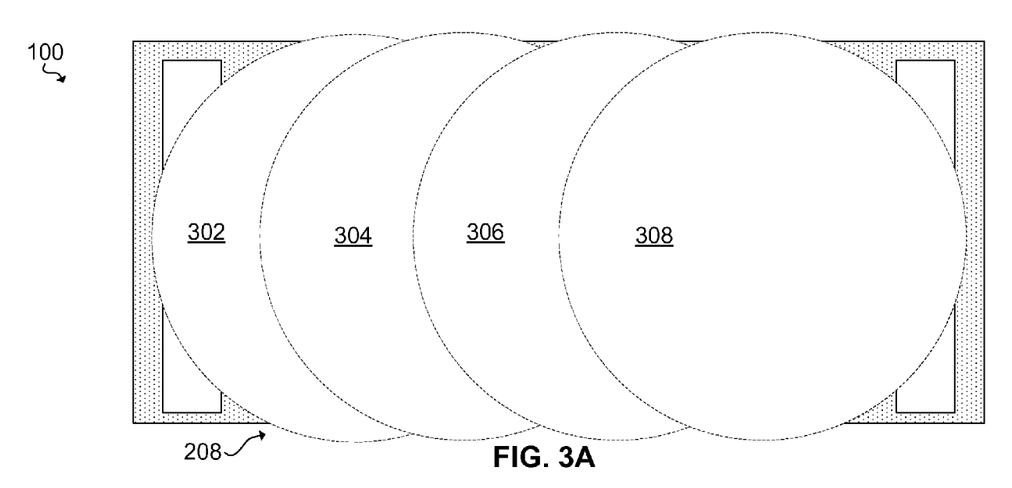
FIG. 3A is a top view of a stepwise measurement technique and FIG. 3B is a cross section view of the stepwise measurement technique, according to an embodiment of the present invention.
Figure 3B:
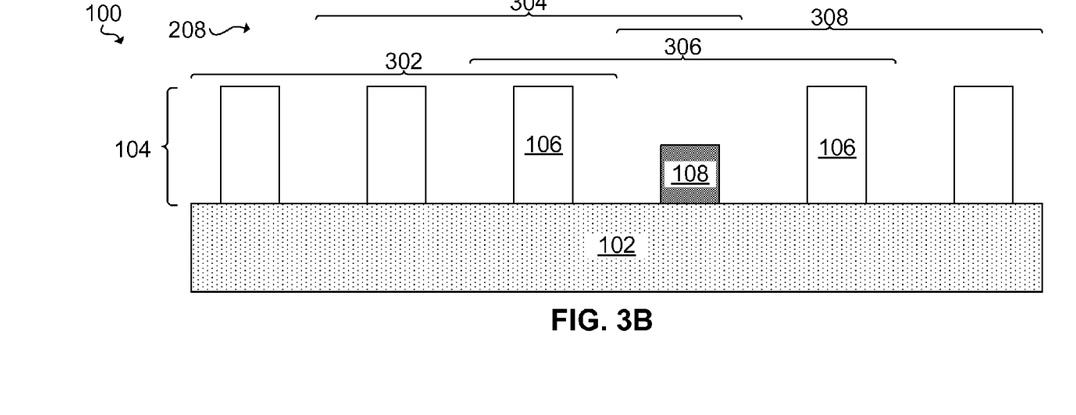

Referring now to FIGS. 3A-3B, a stepwise measurement technique using the metrology tool 200 is shown. FIG. 3A illustrates a top view of the stepwise measurement technique. FIG. 3B illustrates a cross section view of the stepwise measurement technique. As the impacting light beam 208 is moved across the area to be scanned, measurements of the reflected light beam 210 (FIG. 2) may be captured along the way by the detector 212 (FIG. 2). In an embodiment, the impacting light beam 208 may be stepped across the area to be measured. With reference to the figure above, the impacting light beam 208 may first be shined on just the area shown as a first step 302 and a record may be made of the data from the reflected light beam 210 captured at the detector. Next, the impacting light beam 208 may be shined on just the area shown as a second step 304 and a record may be made of the data from the reflected light beam 210 captured at the detector. The same may be done for the area denoted by a third step 306, and then for the area denoted by a fourth step 308.

In an embodiment, the step size of each measurement may be approximately 1 pitch of the features to be measured. Each step may overlap the previous step. The more steps conducted (i.e., more data collected) and the more overlap between each step, the more accurate the results of the measurements may be. Accordingly, embodiments are contemplated in which the step size is less than approximately 1 pitch of the features to be measured. However, embodiments are also considered in which the step size is more than approximately 1 pitch of the features to be measured.

Although the steps are illustrated moving perpendicular to the length of the fins 104, embodiments are considered in which the steps may move parallel or diagonally with the length of the fins. The metrology tool 200 may be advanced stepwise over the desired area and the structure 100 may remain stationary. In another embodiment, the metrology tool 200 may remain stationary and the structure 100 may be moved below it to measure the desired area. In yet another embodiment, both the metrology tool 200 and the structure 100 may be moved.

According to embodiments of the present invention, the data from the reflected light beam 210 captured at each step may be converted to data that approximates the characteristics of the features. This may be done using models that each indicate what the reflected light should look like at the detector after being calibrated with features having known characteristics. After completing the scan across the desired area (i.e., across all of the steps), a novel analysis may be done to obtain the characteristics of the structure. In a preferred embodiment, linear systems of equations may be solved to determine the measurements of the constituent features.

The data from the collected beam 210 captured from each step may be converted to provide an average value of a chosen parameter or parameters of the features in that individual area. In an embodiment, the conversion may be done using one or more linear equations and may be conducted using computer hardware built into the metrology tool 200 or using separate computer hardware.

For example, the first step 302 may measure an area including three tall fins 106, each having a height of approximately 10 nm. The average height of features in the first step 302 would be the sum of the heights of the individual fins divided by the number of features of the first step 302. In other words, the average height $H_{302}$ for the first step 302 would be 10 nm:

$$H_{302} = \frac{1}{3}(10+10+10) = 10 \tag{1}$$

The average height $H_{304}$ for the second step 304 would be 8.33 nm:

$$H_{304} = \frac{1}{3}(10+10+5) = 8.33 \tag{2}$$

Accordingly, the average height $H_{306}$ of the third step 306 and average height $H_{308}$ of the fourth step 308 would each also be 8.33 nm. Taking an average of the heights of these steps would give an overall average height $H_{avg}$ of 8.75 nm:

$$H_{avg} = \frac{1}{4}(10+8.33+8.33+8.33) = 8.75 \tag{3}$$

Another way of expressing the $H_{avg}$ may be:

$$H_{avg} = \frac{1}{3}\begin{pmatrix} 1 & 1 & 1 & 0 & 0 & 0 \\ 0 & 1 & 1 & 1 & 0 & 0 \\ 0 & 0 & 1 & 1 & 1 & 0 \\ 0 & 0 & 0 & 1 & 1 & 1 \end{pmatrix} \begin{pmatrix} a \\ b \\ c \\ d \\ e \\ f \end{pmatrix} = \begin{pmatrix} 10 \\ 8.33 \\ 8.33 \\ 8.33 \end{pmatrix} \tag{4}$$

in which the variables a through f represent the individual heights of each fin 104. It should be noted that this is an underdetermined system of equations and due to the incomplete circulant nature of the kernel, the values will not be equal to the exact measurements, and the values of areas on the edge of the desired area to be measured will be less accurate due to be measured with less steps than interior areas. As the number of scans and the number of steps increases, the results converge to the actual parameters of the features.

In general, the system of equations illustrated above may be described as a linear equation:

$$Ax = y, \text{ wherein:} \tag{5}$$

$$A \in R^{(m*n)}. \tag{6}$$

In the above equations, m is the number of scans and n=p+m−1, wherein p is the number of pitches in the desired measuring area. In addition, x is a vector with the target parameter in each step of the beam, y is a vector of the results of each scan, and A is a semi-circulant matrix with only p unique elements, represented below:

$$\begin{pmatrix} a_1 & \dots & a_p & \dots & 0 & 0 \\ 0 & a_1 & \dots & a_p & \dots & 0 \\ 0 & 0 & a_1 & \dots & a_p & \dots \end{pmatrix} \tag{7}$$

The elements of A may not be equal to one another and may be dependent on the illumination profile and position of the feature in relation to the center of illumination. Because of these constraints, the edge terms must necessarily converge to 0. The elements of A can be determined by measuring a known structure or a calibration structure that will be sampled by a reference technique, such as, for example, TEM or SEM. During the calibration procedure, the kernel can be generalized as a spatial distribution function in one or two dimensions, where a continuous interpolation can be done. In embodiments in which the step size does not match the pitch of the features on the structure, the interpolated values may be used.

Because of the multiple parameters that can be measured using inverse measurement techniques, multiple systems of equations such as $$Ax_i = y_i \qquad (8)$$

may be incorporated, wherein i refers to all the different parameters that can be extracted using the metrology technique.

Figure 4:
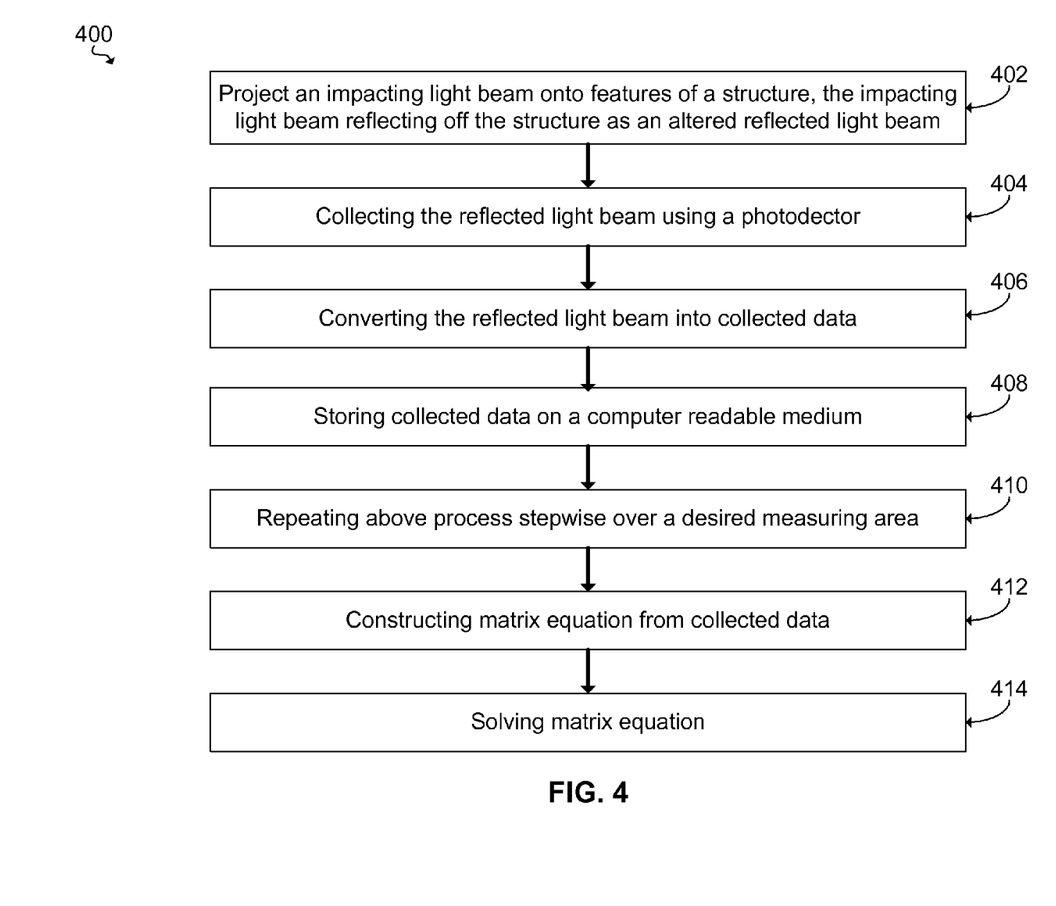
FIG. 4 is a flow diagram for the stepwise measurement technique using the metrology tool, according to an embodiment of the present invention.

Referring now to FIG. 4, a flow diagram 400 for an embodiment of the stepwise measurement technique using the metrology tool 200 is shown. It should be noted that the process of FIG. 4 is described with the aid of the top view of the stepwise measurement technique in FIG. 3A and the cross section view of the stepwise measurement technique in FIG. 3B.

At 402, the light source 202 of the metrology tool 200 may project the impacting light beam 208, optionally using the reticle 206, onto the fins 104 of the structure 100. In 404, the reflected light beam 210 may be collected by the photodetector 212. In 406, the reflected light beam 210 may be converted to collected data by a light processing unit (not shown). The light processing unit may be implemented as software, firmware, hardware, or any combination thereof. In 408, the collected data may be stored on a computer readable medium as described above. In 410, the previous steps 402-408 may be repeated, stepwise as described above, over an entire desired measuring area. In 412, the collected data may be constructed into a set of linear equations in a matrix using a compiling unit (not shown). The compiling unit may be implemented as software, firmware, hardware, or any combination thereof. In 414, the constructed set of linear equations in a matrix may be solved to provide measurements using a calculation unit (not shown). The calculation unit may be implemented as software, firmware, hardware, or any combination thereof. In an optional step (not shown) the measurements may be stored in a computer readable medium and displayed to a user.

Figure 5:
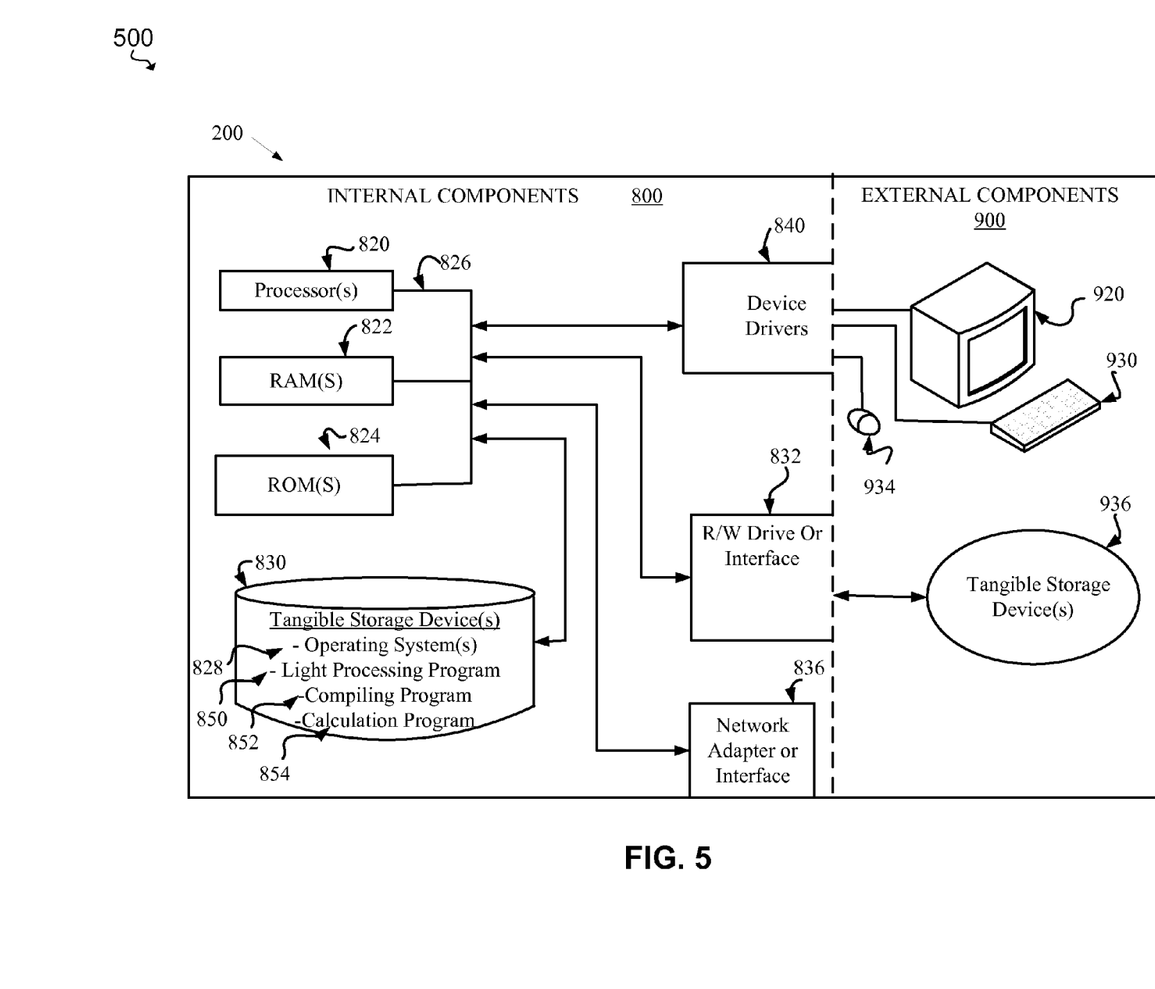
FIG. 5 is a block diagram of components of a data processing system such as the metrology tool, according to an embodiment of the present invention.

Referring to FIG. 5, a block diagram 500 of components of a data processing system 800, 900, such as the metrology tool 200 is shown in accordance with an illustrative embodiment of the present invention. It should be appreciated that FIG. 5 provides only an illustration of one implementation and does not imply any limitations with regard to the environments in which different embodiments may be implemented. Many modifications to the depicted environments may be made based on design and implementation requirements.

Data processing system 800, 900 is representative of any electronic device capable of executing machine-readable program instructions. Data processing system 800, 900 may be representative of a smart phone, a computer system, PDA, or other electronic devices. Examples of computing systems, environments, and/or configurations that may be represented by data processing system 800, 900 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The metrology tool 200 may include respective sets of internal components 800 and external components 900. The internal components 800 may include one or more processors 820, one or more computer-readable RAMs 822 and one or more computer-readable ROMs 824 on one or more buses 826, and one or more operating systems 828 and one or more computer-readable tangible storage devices 830. The one or more operating systems 828 and programs such as a light processing program 850 corresponding to the light processing unit, a compiling program 852 corresponding to the compiling unit, and a calculation program 854 corresponding to the calculation unit may be stored on one or more computer-readable tangible storage devices 830 for execution by one or more processors 820 via one or more RAMs 822 (which typically include cache memory).

In the embodiment illustrated in FIG. 5, each of the computer-readable tangible storage devices 830 may be a magnetic disk storage device of an internal hard drive. Alternatively, each of the computer-readable tangible storage devices 830 may be a semiconductor storage device such as ROM 824, EPROM, flash memory or any other computer-readable tangible storage device that can store a computer program and digital information.

The internal components 800 may also include a R/W drive or interface 832 to read from and write to one or more portable computer-readable tangible storage devices 936 such as a CD-ROM, DVD, memory stick, magnetic tape, magnetic disk, optical disk or semiconductor storage device. The light processing program 850, the compiling program 852, and the calculation program 854 may be stored on one or more of the respective portable computer-readable tangible storage devices 936, read via the respective R/W drive or interface 832 and loaded into the respective hard drive 830.

The internal components 800 may also include network adapters (or switch port cards) or interfaces 836 such as a TCP/IP adapter cards, wireless wi-fi interface cards, or 3G or 4G wireless interface cards or other wired or wireless communication links. The light processing program 850, the compiling program 852, and the calculation program 854 may each be downloaded to the metrology tool 200 from an external computer (e.g., server) via a network (for example, the Internet, a local area network or other, wide area network) and respective network adapters or interfaces 836. From the network adapters (or switch port adaptors) or interfaces 836, the light processing program 850, the compiling program 852 and the calculation program 854 may be loaded into the respective hard drive 830. The network may comprise copper wires, optical fibers, wireless transmission, routers, firewalls, switches, gateway computers and/or edge servers.

The external components 900 may include a computer display monitor 920, a keyboard 930, and a computer mouse 934. The external components 900 may also include touch screens, virtual keyboards, touch pads, pointing devices, and other human interface devices. The internal components 800 may also include device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Embodiments of the present invention may provide more accurate measurements of characteristics of semiconductor features over a large area of a semiconductor structure than conventional direct or indirect metrology techniques. This may allow for a better comparison of the measured characteristic to a predetermined desired value for quality control purposes. If the measured characteristic varies from the predetermined desired value by more than a predetermined amount, the semiconductor structure may be discarded. Applications of the present invention may also be used to improve process control. The more accurate data gathered from the stepwise metrology technique can be used to tune and optimize the process for ideal uniformity of the desired characteristic. In addition, applications of the present invention may be used in defect pattern detection. The accurate localized data that may be gathered using the stepwise metrology method may allow for improved systematic/nonsystematic defect determination.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method of measuring an average characteristic of features on a semiconductor structure comprising:
    projecting a light beam onto the features in a first area;
    collecting a first reflected light beam from the first area, wherein the first reflected light beam is the projected light beam after it has reflected off the features in the first area;
    converting the first reflected light beam into first data;
    projecting the light beam onto the features in a second area, wherein the second area overlaps with the first area by at least one individual feature;
    collecting a second reflected light beam from the second area, wherein the second reflected light beam is the projected light beam after it has reflected off the features in the second area;
    converting the second reflected light beam into second data;
    performing analysis of the first data and second data to determine an overall average value;
    comparing the overall average value to a predetermined desired value; and
    discarding the semiconductor structure if the overall value differs from the desired value by a predetermined amount.

2. The method of claim 1, wherein the light beam has a width that is larger than a width of the individual features.

3. The method of claim 1, wherein the analysis comprises:
    setting up a first linear equation comprising a first weighted average of the characteristic of the features in each of the first area;
    setting up a second linear equation comprising a second weighted average of the characteristic of the features in each of the first area;
    combining the first linear equation and the second linear equation into a system of equations; and
    solving the system of equations.

4. The method of claim 3, wherein the system of equations comprises a linear equation $Ax=y$, wherein $A \in R^{(m*n)}$, m is the number of areas, $n=p+m-1$, p is the number of pitches overall, x is a vector with the characteristic in each area, y is the weighted average in each area, and A is a semi-circulant matrix with only p unique elements, $$\begin{pmatrix} a_1 & \ldots & a_p & \ldots & 0 & 0 \\ 0 & a_1 & \ldots & a_p & \ldots & 0 \\ 0 & 0 & a_1 & \ldots & a_p & \ldots \end{pmatrix}.$$

5. The method of claim 1, wherein the projecting the light beam onto the features in the second area comprises moving the light beam by approximately 1 pitch of the features.

6. The method of claim 1, wherein the projecting the light beam onto the features in the second area comprises moving the semiconductor structure by approximately 1 pitch of the features.

7. A non-transitory computer program product for measuring an average characteristic of features on a semiconductor structure, the computer program product comprising a computer readable storage medium readable by a processing circuit and storing instructions for execution by the processing circuit for performing a method comprising:
    projecting a light beam onto the features in a first area;
    collecting a first reflected light beam from the first area, wherein the first reflected light beam is the projected light beam after it has reflected off the features in the first area;
    converting the first reflected light beam into first data;
    projecting the light beam onto the features in a second area, wherein the second area overlaps with the first area by at least one individual feature;
    collecting a second reflected light beam from the second area, wherein the second reflected light beam is the light beam after it has reflected off the features in the second area;
    converting the second reflected light beam into second data;
    performing analysis of the first data and second data to determine an overall average value;
    comparing the overall average value to a predetermined desired value; and
    discarding the semiconductor structure if the overall value differs from the desired value by a predetermined amount.

8. The non-transitory computer program product of claim 7, wherein the light beam has a width that is larger than a width of the individual features.

9. The non-transitory computer program product of claim 7, wherein the analysis comprises:
    setting up a first linear equation comprising a first weighted average of the characteristic of the features in each of the first area;
    setting up a second linear equation comprising a second weighted average of the characteristic of the features in each of the first area;
    combining the first linear equation and the second linear equation into a system of equations; and
    solving the system of equations.

10. The non-transitory computer program product of claim 9, wherein the system of equations comprises a linear equation $Ax=y$, wherein $A \in R^{(m*n)}$, m is the number of areas, $n=p+m-1$, p is the number of pitches overall, x is a vector with the characteristic in each area, y is the weighted average in each area, and A is a semi-circulant matrix with only p unique elements, $$\begin{pmatrix} a_1 & \ldots & a_p & \ldots & 0 & 0 \\ 0 & a_1 & \ldots & a_p & \ldots & 0 \\ 0 & 0 & a_1 & \ldots & a_p & \ldots \end{pmatrix}.$$

11. The non-transitory computer program product of claim 7, wherein the projecting the light beam onto the features in the second area comprises moving the light beam by approximately 1 pitch of the features.

12. The non-transitory computer program product of claim 7, wherein the projecting the light beam onto the features in the second area comprises moving the semiconductor structure by approximately 1 pitch of the features.

13. A computer system for measuring an average characteristic of features on a semiconductor structure comprising:
   a memory;
   a processor comprising a hardware and in communication with the memory, the processor comprising an instruction fetching unit for fetching instructions from memory and one or more execution units for executing fetched instructions;
   wherein said computer system is capable of performing a method comprising:
      projecting a light beam onto the features in a first area;
      collecting a first reflected light beam from the first area, wherein the first reflected light beam is the light beam after it has reflected off the features in the first area;
      converting the first reflected light beam into first data;
      projecting the light beam onto the features in a second area, wherein the second area overlaps with the first area by at least one individual feature;
      collecting a second reflected light beam from the second area, wherein the second reflected light beam is the light beam after it has reflected off the features in the second area;
      converting the second reflected light beam into second data; and
      performing analysis of the first data and second data to determine an overall average value;
   wherein the analysis comprises:
      setting up a first linear equation comprising a first weighted average of the characteristic of the features in each of the first area;
      setting up a second linear equation comprising a second weighted average of the characteristic of the features in each of the first area;
      combining the first linear equation and the second linear equation into a system of equations; and
      solving the system of equations.

14. The computer system of claim 13, wherein the light beam has a width that is larger than a width of the individual features.

15. The computer system of claim 13, wherein the projecting the light beam onto the features in the second area comprises moving the light beam by approximately 1 pitch of the features.

16. The computer system of claim 13, wherein the projecting the light beam onto the features in the second area comprises moving the semiconductor structure by approximately 1 pitch of the features.

17. The computer system of claim 13, wherein the system of equations comprises a linear equation $Ax=y$, wherein $A \in R^{(m*n)}$, m is the number of areas, $n=p+m-1$, p is the number of pitches overall, x is a vector with the characteristic in each area, y is the weighted average in each area, and A is a semi-circulant matrix with only p unique elements, $$\begin{pmatrix} a_1 & \ldots & a_p & \ldots & 0 & 0 \\ 0 & a_1 & \ldots & a_p & \ldots & 0 \\ 0 & 0 & a_1 & \ldots & a_p & \ldots \end{pmatrix}.$$

* * * * *